US011931245B2

(12) United States Patent
Bayer

(10) Patent No.: US 11,931,245 B2
(45) Date of Patent: Mar. 19, 2024

(54) INJECTOR FOR INTRAOCULAR LENSES

(71) Applicant: OPHTHALMO PRO GMBH, Sankt Ingbert (DE)

(72) Inventor: Alexander Bayer, Düsseldorf (DE)

(73) Assignee: OPHTHALMO PRO GMBH (DE)

( * ) Notice: Subject to any disclaimer, the term of this patent is extended or adjusted under 35 U.S.C. 154(b) by 0 days.

(21) Appl. No.: 18/024,331

(22) PCT Filed: Sep. 4, 2020

(86) PCT No.: PCT/EP2020/074776
§ 371 (c)(1),
(2) Date: Mar. 2, 2023

(87) PCT Pub. No.: WO2022/048767
PCT Pub. Date: Mar. 10, 2022

(65) Prior Publication Data
US 2023/0285139 A1    Sep. 14, 2023

(51) Int. Cl.
*A61F 2/16* (2006.01)
(52) U.S. Cl.
CPC .................. *A61F 2/1672* (2013.01)
(58) Field of Classification Search
CPC ........ A61F 2/16; A61F 2/1672; A61F 2/1662; A61F 2/1667; A61F 2/167; A61F 2/1675; A61F 2/1678; A61F 2/1691
See application file for complete search history.

(56) References Cited

U.S. PATENT DOCUMENTS

| | | | |
|---|---|---|---|
| 4,810,249 A | 3/1989 | Haber | |
| 6,106,496 A * | 8/2000 | Arnissolle | A61M 25/10182 604/207 |
| 8,105,332 B2 | 1/2012 | Downer et al. | |
| 9,326,848 B2 | 5/2016 | Woods | |
| 2009/0112223 A1* | 4/2009 | Downer | A61F 2/1667 606/107 |
| 2016/0128752 A1 | 5/2016 | Greter | |

FOREIGN PATENT DOCUMENTS

| | | |
|---|---|---|
| CN | 202021009293 U | 6/2020 |
| CN | 202010500344 A | 12/2021 |
| EP | 3476375 A1 | 5/2019 |
| WO | 2019195951 A1 | 10/2019 |

* cited by examiner

*Primary Examiner* — Vi X Nguyen
(74) *Attorney, Agent, or Firm* — DINSMORE & SHOHL LLP

(57) ABSTRACT

An intraocular lens implantation injector has a base body and an elongated actuation element projecting into a base body rear section and movably guided along an actuation axis. Actuation element movement is generated selectively by axial push actuation or by a screw actuation about the axis. The actuation element features an external thread at least on one section. At least one spring arm arranged at the base body has an inner surface thread engagement structure facing the external thread. A switch element, interacting with the spring arm, is rotatably or displaceably arranged on the base body. The switch element interacts with the spring arm via an operative contact. At least one switch element inner surface and/or spring arm outer surface involved in the operative contact is angularly inclined to the axis. Switch element rotation/displacement generates spring arm elastic deformation towards/away from the axis, thereby engaging/disengaging the thread engagement structure.

14 Claims, 6 Drawing Sheets

INJECTOR FOR INTRAOCULAR LENSES

CROSS-REFERENCE TO RELATED APPLICATIONS

This application is the U.S. National Stage of PCT/EP2020/074776 filed on Sep. 4, 2020, the entire content is incorporated herein by reference in its entirety.

FIELD OF THE INVENTION

The invention relates to an injector for implantation of an intraocular lens, having a base body and an elongated actuation element, which projects at least partly into a rear section of the base body and which is movably guided in an actuation axis, and whereas a movement of the actuation element into the base body can be generated selectively by means of a push actuation along the actuation axis or by means of a screw actuation about the actuation axis, and whereas the actuation element features an external thread at least on one section.

BACKGROUND OF THE INVENTION

Injectors for the implantation of intraocular lenses into a human eye are well known. For this purpose, an intraocular lens can either be inserted into the injector via a lens cartridge with an intraocular lens inserted into it shortly before the lens is inserted into the eye, in order to expel the intraocular lens from an anterior ejection nozzle into the posterior chamber of the eye after subsequent addition of a viscoelastic medium. The ejection nozzle forms the open end of a lens guide of the injector, which is located at the front of the base body.

In the base body, a piston is movably guided along the actuation axis, and the piston, which is connected to the actuation element in front of each other along the actuation axis, can come into contact with the intraocular lens and expel it through the ejection nozzle when the actuation element is advanced and thus transferred to the piston in the direction of the ejection nozzle.

In order to move the piston in a controlled manner within the base body of the injector and, advancing further in the direction of the ejection nozzle, also through the lens guide section, the actuation element is provided, which projects into the base body in such a way that, when the actuation element is advanced in the actuation axis, the piston first contacts the intraocular lens and can then be moved together with the intraocular lens in the direction of the ejection nozzle until the intraocular lens is ejected into the posterior eye chamber. Injectors of the newer type are used as disposable injectors and are disposed of after single use and ejection of the pre-loaded intraocular lens. This type of injector is generally referred to as pre-load system.

Advancing the actuation element into a rear opening in the base body is usually done manually by the operator, i.e. the ophthalmologist. Injectors are known, which, in a first operating mode enable a pure pushing movement, which pushing movement is manually introduced into the actuation element, and, in a second operating mode, a rotary movement is enabled, which is introduced into the same actuation element in order to move the actuation element along the actuation axis in the same way. In this respect, injectors of newer design are capable of both push and screw actuation, for which purpose a corresponding device for switching the operating mode is provided on the injector.

For example, EP 3 476 375 A1 reveals an injector for the implantation of an intraocular lens, and the actuation element can be driven into the base body either by pushing or by a screw movement, whereas the screw movement can be manually introduced into a rotating element, which has a direct threaded connection with an external thread of the actuation element. If, however, the actuation element is manually pushed into the base body, in the rotating element is caused a free rotating movement. If the rotating element is driven into the base body either by pushing on the back of the actuation element or by manually turning the rotating element, the actuation element can drive the intraocular lens in contact with the piston out of the ejection nozzle at the front end.

The WO 2019/195951 A1 reveals another design of an injector for the implantation of an intraocular lens into a human eye, having a base body into which an elongated actuation element projects in sections at the rear and is movably guided in an actuation axis, and whereas a movement of the actuation element into the base body can be produced optionally by means of a push actuation of the actuation element along the actuation axis or by means of a screw actuation of the actuation element about the actuation axis, for which purpose the actuation element features an external thread at least on one section. In order to switch over between the push actuation and the screw actuation of the actuation element, two opposite folding and unfolding wing handles are provided, whereas the unfolded position allows the operating mode to be switched to push actuation and in a folded position to screw actuation. In the operating mode of the push actuation the foldable wing handles can be used as finger grips, so that an operator can grip the injector at the wing handles between the index finger and the middle finger, in order to finally push the actuation element into the base body with the thumb at the back. Once the wing handles are folded, the actuation element can be screwed into the base body by holding the base body in a first hand of the operator and screwing the actuation element with the second hand of the operator.

Adjustment of the injector for either push or screw actuation is usually performed by a medical assistant, and then the ophthalmologist applies the injector in the preset mode by inserting the ejector nozzle into the eyeball at the anterior lens guide section and then actuating the actuation element until the intraocular lens is driven into the posterior eye chamber.

SUMMARY OF THE INVENTION

The purpose of the invention is the further development of an injector for the implantation of an intraocular lens into a human eye, whereas the injector should exhibit the simplest possible switchability between the push actuation and the screw actuation of the actuation element for advancing the intraocular lens. In particular, it shall be possible to switch the operating mode between the push actuation and the screw actuation in such a way that the injector is otherwise to be used in the same way, but whereas the switchover between the push actuation and the screw actuation should be adjustable immediately before the injector is used.

This objective is solved starting from an injector according to the generic term disclosed herein in combination with the characteristic features. Advantageous embodiments of the invention are also disclosed.

The invention relates to the technical teaching that at least one spring arm is arranged on the base body, whereas the spring arm features a thread engagement structure on an inner surface facing the external thread, whereas the switch element interacts with the spring arm and is rotatable about the actuation axis or displaceable in the actuation axis, and whereas the switch element interacts with the spring arm via an operative contact, whereas at least one inner surface of the switch element involved in the operative contact and/or an outer surface of the spring arm involved in the operative contact is formed inclined at an angle to the actuation axis, so that upon rotation or upon displacement of the switch element an elastic deformation of the spring arm towards the actuation axis and away from the actuation axis can be generated, whereby the thread engagement structure can be selectively engaged or disengaged with the external thread.

The core idea of the invention is a switch element, which can be manually rotated or displaced between two actuation positions, and in a first actuation position the switch element causes the thread engagement structure on the spring arm to engage with the external thread of the actuation element for screw actuation, and in the second actuation position the switch element releases the spring arm with the thread engagement structure from the external thread of the actuation element, so that the spring arm is disengaged from the external thread of the actuation element, and the actuation element is finally freely displaceable for push actuation.

Thus, if the switch element is rotated into the second actuation position, the spring arm or several spring arms, especially two spring arms arranged opposite to each other, can spring outward elastically by themselves, so that the thread engagement structure releases the external thread of the actuation element. According to the invention, the interaction connection between the switch element and the spring arm is formed by an interaction or operative contact, which is set up in such a way that, in the event of an axial displacement of the switch element relative to the spring arm, a movement of the spring arm is generated, which occurs in a radial direction with respect to the actuation axis, namely that the spring arm can be moved towards the actuation axis and thus towards the external thread of the actuation element and the other way around away from it again. Therein, the axial direction describes a direction extending along the actuation axis and a radial direction describes a direction perpendicular to the actuation axis. In this respect, the axial and radial directions are perpendicular to each other.

In order to generate the movement in the spring arm by a movement of the switch element, at least one surface involved in the interaction or operation contact features an inclination, which features an angle to the extension of the actuation axis. The angle can be measured between the actuation axis and a vector lying in the operative surface, i.e. the inner surface and/or the outer surface, whereas the vector runs through the contact point or the contact line between the inner surface and the outer surface. Of course, the inner surface of the switch element and/or the outer surface spring arm may also be curved or otherwise may deviate from a plane without deviating from the inventive idea of an interaction contact at an angle.

The inclination of the involved surface can be the inner surface of the switch element, while the outer surface of the spring arm is straight, i.e. extending in the direction of the actuation axis without an angle, while the outer surface is accordingly inclined or curved.

In the same way, the outer surface of the spring arm can be straight and the inner surface of the switch element is inclined or curved.

Of course, the principle of interaction between the switch element and the spring arm, according to the invention, works particularly well if both the inner surface and the outer surface feature an inclination or a curvature, which, in particular, each enclose the same angle with the actuation axis. In any embodiment of the inner surface and the outer surface, however, there is an interaction contact, which is inclined at an angle relative to the actuation axis. The switch element does not have to be fabricated in one piece, but can also be made from multiple pieces, so that the inner surface can also be formed on a part of the switch element, which cannot be operated manually from the outside.

Another advantage is that the surfaces involved in the interaction contact can feature a coating, which allows the surfaces to slide against each other particularly well, and therefore the inner and/or outer surfaces feature the coating.

For example, the switch element is designed as a pushing element and is movably arranged in or on the base body. The inner surface of the pushing element can be designed in such a way, that it moves relative to the spring arm when the pushing element on the base body is displaced, and the principle of the interaction contact at an angle to the actuation axis can therefore also be used for a pushing element. In a preferred embodiment, the switch element is designed ring-shaped or hull-shaped and encloses the actuation element partially or completely.

If the switch element is designed ring-shaped or hull-shaped, it is preferably arranged on the base body in such a way, that the axis of rotation of the ring-shaped or hull-shaped switch element coincides with the actuation axis.

The handling of the injector with a rotatable switch element is generally easier and more comfortable than displacing a displacement element between two detent positions. However, it is also conceivable that a ring-shaped or hull-shaped switch element can also be displaced in the actuation axis on the base body, i.e. it can be moved between two detent positions.

Moreover, it is conceivable that the switch element features a pushing-rotating-movability in arrangement at the base body, which represents the most preferred embodiment, namely when the switch element can be displaced at the base body with a thread-like guiding between the switch element and the base body. If the switch element then is rotated manually and the contact between the switch element and the body is established by a corresponding thread-like guiding, the axial displacement of the switch element in the actuation axis can be caused very conveniently.

In particular, the switch element forms a body of rotation, which can be rotated manually about the actuation axis and which features an internal passage, into which the at least one spring arm projects and through which the actuation element extends. Thus, the spring arm is at least in sections located in a radially formed gap, in particular an annular gap, formed in between the outer surface of the actuation element and the inner surface of the switch element which is surrounding the actuation element.

With further advantage, the inner surface is formed in the internal passage of the switch element and forms an inner cone circumferential about the actuation axis. Thus, if the switch element is displaced in the actuation axis, the outer surface at the spring arm comes into contact with different sections and thus with different radii of the inner surface of the switch element, and due to the inclination caused by the conical structure, these sections either push the spring arm towards the actuation element or increase the distance to the actuation element again, depending on whether the switch element is moved axially into a first or into a second direction. This movement of the switch element in the actuation axis can be superimposed by a rotational movement of the switch element about the actuation axis.

A further advantage is achieved if the base body features a receiving section with a passage, through which the actuation element extends and whereas the actuation element is movably received at or on the receiving section in a rotatable or displaceable manner.

The switch element is guided at or on the receiving section so as to be axially movable along the actuation axis and/or rotatable about the actuation axis, whereas a rear section of the switch element projects backwards beyond the receiving section, in which the inner surface inclined at an angle is formed inside the switch element, which interacts with the at least one spring arm.

Furthermore, at least one spring arm, two spring arms facing each other, three, four or more spring arms can be arranged on the rear side of the receiving section or within the receiving section or at the base body, which protrude inside from the open end of the hull-shaped receiving section and interact with the inner surface of the switch element.

If, for example, several spring arms are arranged, in particular equally distributed over the circumference between the actuation element on the inside and the switch element on the outside, a configuration according to a collet chuck can be achieved, whereas, if several spring arms are arranged around the actuation element and its external thread, the resulting internal thread is formed almost completely from the several thread engagement structures of the spring arms equally distributed over the circumference.

However, it is also technically possible to design the injector with a single spring arm at a circumferential position, for example, if the actuation element is held opposite this single spring arm with the external thread in a bearing shell opposite the spring arm. Such an embodiment is advantageous, if the switch element is designed as a single displacement switch, which is arranged at only one circumferential position.

In order to create a crank mechanism, due to which the switch element moves in the actuation axis at the same time when a rotational movement is manually introduced into the switch element, i.e. a linear movement is superimposed on the rotational movement, it is possible with particular advantage to provide at least one groove in the outer circumference of the receiving section, whereas at least one pin is formed on the inside of the switch element, whereas the pin is guided in the groove. With this groove-pin connection a kind of crank mechanism is created, whereas the groove is preferably spirally formed over a section or the full circumference of the receiving section. For example, the switch element can be rotated through an angle of 90° or 180° about the actuation axis, so that the switch element thereby undergoes an axial displacement in the actuation axis, which is so large that by the interaction contact at the angle of the outer surface or inner surface of the spring arm or of the switch element the spring arm is pressed sufficiently far into the external thread of the actuation element, that a screw connection can be generated between the thread engagement structure of the spring arm and the external thread of the actuation element. With particular advantage, two opposing grooves or three grooves equally distributed around the circumference are provided in a helical configuration in the outer circumference of the receiving section, in which associated pins can run, which are formed on the inside of the inner surface of the switch element. This area of the inner surface of the switch element, which extends over the receiving section, adjoins the area, in which the inclined surface is formed in the inner surface, in particular the inner cone.

In a particular advantageous embodiment, the switch element is arranged on the receiving section by means of a threaded connection, so that upon rotation of the switch element about the actuation axis, the switch element executes a movement along the actuation axis.

Furthermore, the base body may feature a wing handle, whereas the receiving section adjoins the rear side of the wing handle as an extension. The receiving section, the wing handle and the further, remaining base body can be designed in one piece and can be made of the same material and thus can be manufactured especially by an injection molding process.

Furthermore, it is advantageous if the injector features a receiving means for a lens cartridge, whereas an intraocular lens is inserted into the lens cartridge, and whereas the lens cartridge with the intraocular lens can be inserted into the receiving means. Such injectors can, in particular, be reusable, provided they can be re-sterilized. However, an injector that can be loaded with a cartridge can also be designed as a disposable article.

The injector can also be designed as a so-called pre-load system, according to which the injector features a receiving chamber, which is formed in the base body and/or in a lens guide section arranged at the front end of the base body, and in which an intraocular lens is inserted, so that the injector forms an individually manageable and tradable unit with the already inserted intraocular lens. In this respect, the injector according to the invention can function as a so called pre-load system or as a cartridge system, alternatively.

Furthermore, a piston is received in the base body and can be displaced axially by the actuation element via a rotary joint. Especially when the screw actuation of the injector is set up, the actuation element has to perform the rotational movement, while the piston only performs a linear movement in the actuation axis without rotating about the actuation axis.

The base body is advantageously formed in one piece with the receiving section and with the wing handle from a plastic body, whereas the lens guide section with a tip-side ejection nozzle for ejecting the intraocular lens is arranged at the front end of the base body.

BRIEF DESCRIPTION OF THE DRAWINGS

Further measures to improve the invention are described in more detail below, together with a description of preferred embodiments of the invention shown in the Figures. It is shown.

DETAILED DESCRIPTION OF THE INVENTION

Figure 1:
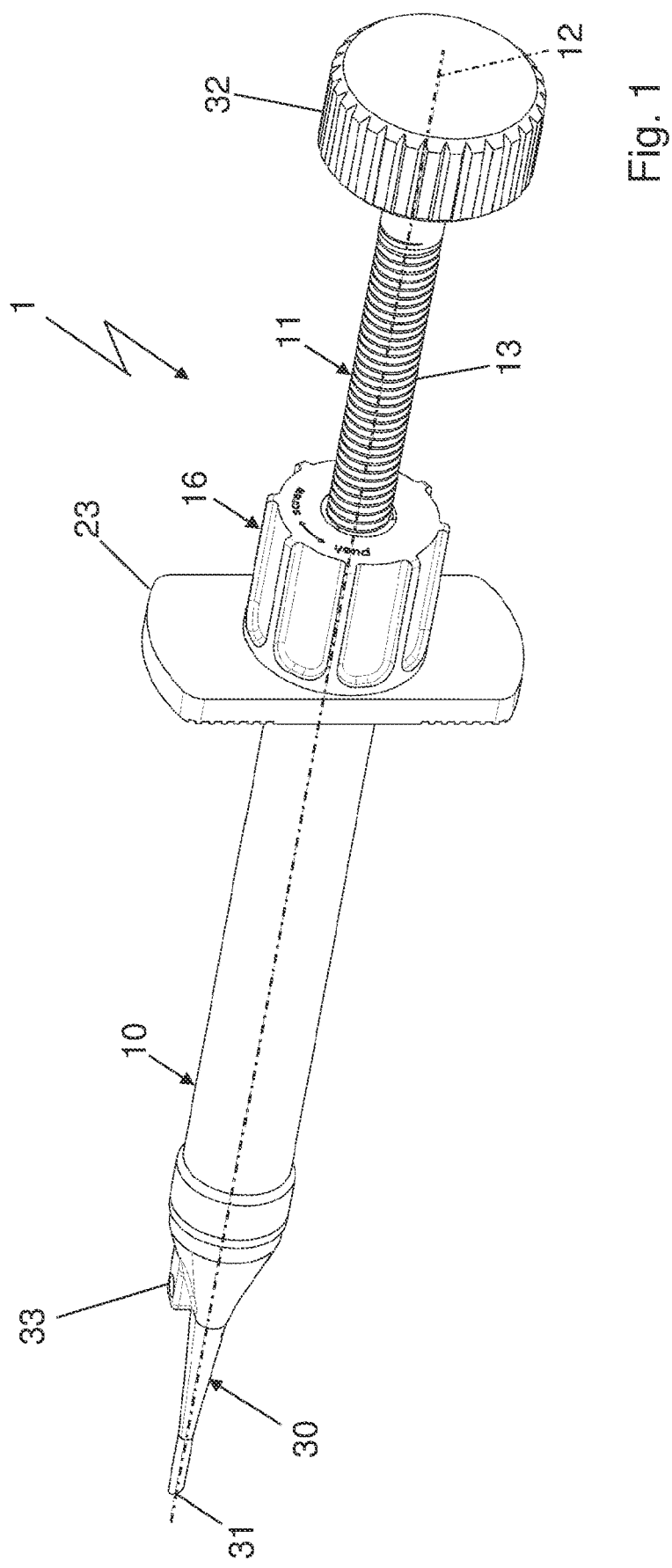
FIG. 1 a perspective view of the injector for implantation of an intraocular lens into a human eye.

FIG. 1 shows a perspective view of the injector 1, which is used to implant an intraocular lens 26 into a human eye. The injector 1 has a base body 10 as its main structural component, and an elongated actuation element 11 with a handle 32 at the rear end is partially inserted into the base body 10. The actuation element 11 has a section with an external thread 13 over its essential length, and the actuation element 11 is inserted in sections from the rear into the base body 10 in such a way that the handle 32 is formed at a free end of the actuation element 11.

At the front side of the base body 10, a lens guide section 30 is arranged in which the intraocular lens 26 is inserted in a manner not shown closer. The main component of the base body 10 is approximately cylindrical or ergonomically designed for handling by a human hand and has an elongated extension, and the injector 1 with the base body 10, with the lens guide section 30 at the front and with the actuation element 11 inserted at the rear extends longitudinally in an actuation axis 12. The actuation axis 12 simultaneously forms the displacement axis and the rotation axis for the optionally displaceable or rotatable actuation element 11.

For an improved handling there is a wing handle 23 on the rear part of the base body 10, so that the injector 1 can be grabbed between the index finger and the middle finger with the wing handle 23, while the thumb can be used to push on the handle 32 on the rear side. At the back of the wing handle 23 follows a switch element 16, which is mounted on the base body 10 so that it can rotate about the actuation axis 12, and the switch element 16 has a passage through which the actuation element 11 extends. The switch element 16 is arranged on the base body 10 in such a way that it has no direct contact with the actuation element 11 and does not interact directly with it, in particular not by a thread connection.

On the lens guide section 30, a load opening 33 is shown through which a viscoelastic medium can be inserted before the injector is operated. The viscoelastic medium then wets the inserted intraocular lens 26 and the inner lumen, especially in the lens guide 30, in order to promote the process of expelling the intraocular lens 26 or to enable the intraocular lens 26 to be expelled without damage.

The switch element 16 of the injector 1 forms a means to switch the operation mode of the injector 1 between a push actuation and a screw actuation. In the embodiment shown in FIG. 1, the switch element 16 is performed to rotate about the actuation axis 12 on the base body 10 for switching the operating mode between the push actuation and the screw actuation. The interaction of the switch element 16 with the actuation element 11 is shown in more detail in the following figures.

Figure 2:
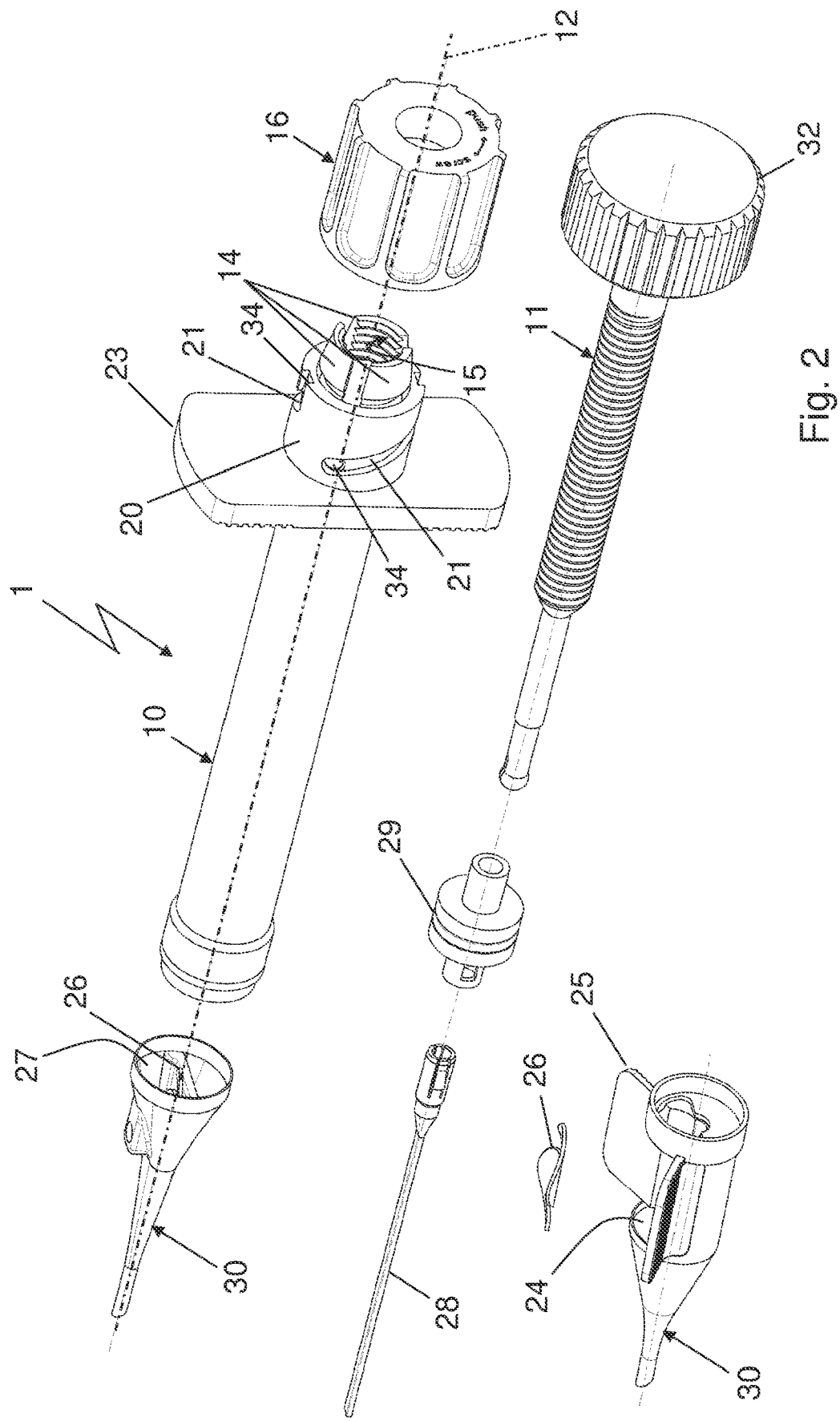
FIG. 2 an exploded view of the main components of the injector as shown in FIG. 1.

FIG. 2 shows the injector 1 in an exploded view, in which the essential parts of the injector 1 are shown. There are further parts of the injector 1, which are not shown, since they are not necessary for the presentation of the present invention, but which shall also be part of the injector 1 according to the invention, so that the illustration is not to be understood conclusively.

The illustration shows the base body 10 separated from the lens guide section 30, and the lens guide section 30, which is shown in alignment with the actuation axis 12, is designed with a receiving chamber 27, in which an intraocular lens 26 is inserted (one of the haptics is visible), and another lens guide section 30, which is shown below, forms an alternative embodiment and features a receiving means 24 for receiving a lens cartridge 25, in which the separated shown intraocular lens 26 can be inserted. If the intraocular lens 26 is inserted into the lens cartridge 25 and the lens cartridge 25 is then inserted into the receiving means 24, the intraocular lens 26 can be expelled from the ejection nozzle 31 at the tip of the lens guide section 30 into the posterior chamber of the human eye by means of a piston 28. If the injector 1 is designed as a pre-load system, the lens guide section 30 shown above can be used, which features a receiving chamber 27 in which the intraocular lens 26 is already inserted by the manufacturer.

To expel the intraocular lens 26, the piston 28 performs a linear movement in the actuation axis 12, and if the actuation element 11 is screwed into the base body 10 by screw actuation, a rotary joint 29 is used to ensure that the rotational movement of the actuation element 11 is not transmitted to the piston 25.

In other words: If the lens guide section 30 is not used with the intraocular lens 26, which is directly inserted in the receiving chamber 27, the lens guide section 30 can be used alternatively, which features the receiving means 24, into which the lens cartridge 25 with an intraocular lens 26 can be inserted. Therein, the lens guide section 30 with the receiving chamber 27 forms the pre-load system, according to which the injector 1 is commercially sold with the intraocular lens 26 already inserted by the manufacturer. Alternatively, the injector 1 can also be sold without the pre-loaded intraocular lens 26, for which purpose the lens guide section 30 features the receiving means 24, into which the lens cartridge 25 with the intraocular lens 26 can only be inserted shortly before the injector 1 is used, which is called a cartridge system. The receiving means 24 for receiving a lens cartridge 25 and/or the receiving chamber 27 for directly receiving an intraocular lens 26 can thus alternatively be arranged in the base body 10, or the receiving means 24 or the receiving chamber 27 are formed in a section between the lens guide section 30 and the base body 10, if the lens guide section 30 has been arranged on the base body 10.

Behind the wing handle 23, the base body 10 features an integrated receiving section 20, to which the switch element 16 is attached rotatably about the actuation axis 12. The outer surface of the receiving section 20 features a groove 21, which is spirally inserted into the receiving section 20, so that when the switch element 16 is rotated about the actuation axis 12, the switch element 16 simultaneously executes a movement in, that means along the actuation axis 12. At the end sections of the groove 21, snapping means 34 can be applied in the groove 21, and if the switch element 16 is rotated into the respective end position, the user obtains a haptic feedback and the switch element 16 automatically remains in the end position. There are pins on the inside of the switch element 16, which are inserted into the groove 21 for an interaction connection with the groove 21. These pins run in the groove 21 and are merely not shown in the figure, so that reference is made to FIG. 3.

The receiving section 20 is hull-shaped and, in particular, is connected in one piece with the base body 10 at the back of the wing handle 23. Exemplarily three spring arms 14 are arranged within the receiving section 20, whereas the spring arms 14 are either rooted elastically on the inside of the receiving section 20 or on the back of the base body 10 or on the wing handle 23. Thus, the spring arms 14 can be resiliently moved radial inwards by elastic deformation towards the actuation axis 12 or outwards away from the actuation axis 12. In a non-forced arrangement of the spring arms 14, these have a distance to each other or to the actuation axis 12, according to which the external thread 13 on the actuation element 11 can be moved freely centrally between the spring arms 14. In the delivery condition of the injector 1, the switch element 16 therefore should be set up in a position allowing push actuation, so that the spring arms 14 are not permanently loaded with force and retain their springback effect over a longer storage period.

An axial displacement of the switch element 16 in the actuation axis 12 produces an elastic spring movement of the spring arms 14 in the direction of the central actuation axis 12, in particular if the switch element 16 is displaced towards the wing handle 23, preferably by rotation, so that the guidance of the groove 21 causes the displacement of the switch element 16 in the actuation axis 12 in the direction towards the wing handle 23. By contact with the inner surface of the switch element 16, the spring arms 14 elastically spring inward towards the actuation axis 12, so that a thread engagement structure 15 on the inside of the spring arms 14 can engage with the external thread 13 of the actuation element 11 to set up the injector 1 for screw actuation accordingly.

Figure 3:
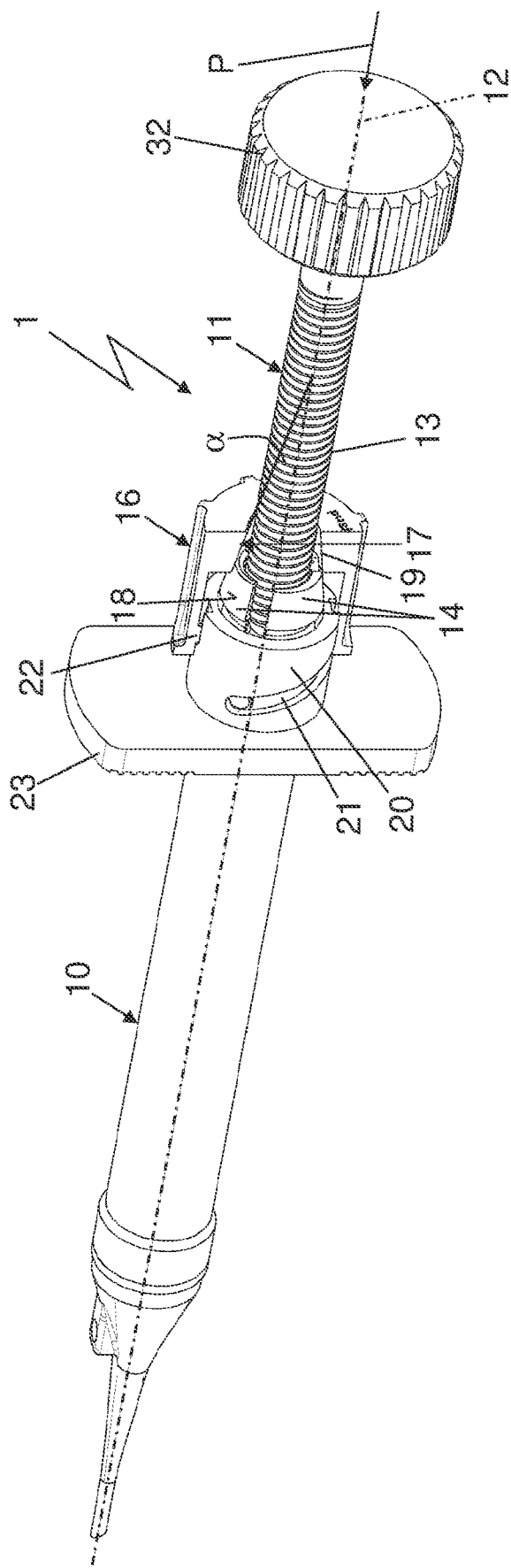
FIG. 3 a perspective view of the injector with a cross-sectional view of the switch element, whereas the switch element is set in a first position, in which the injector can be operated by push actuation.
Figure 4:
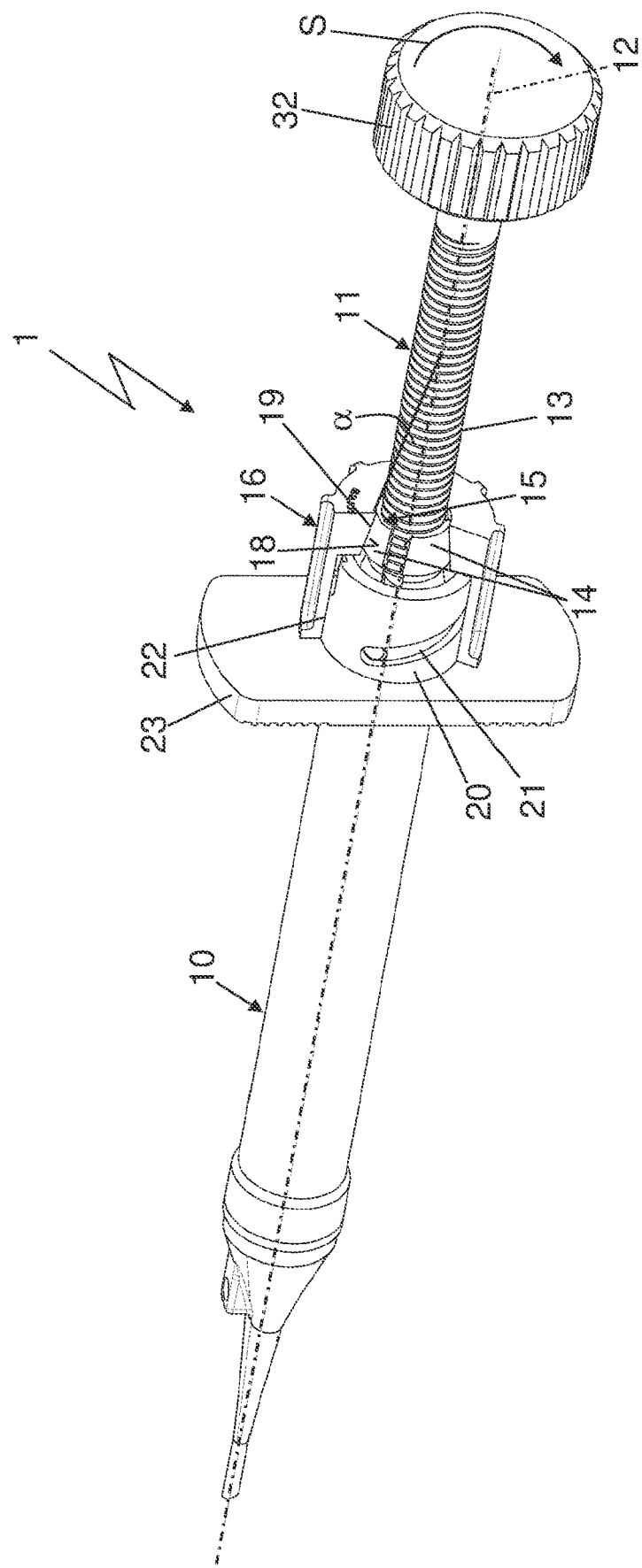
FIG. 4 the perspective view of the injector with a cross-sectional view of the switch element, whereas the switch element is set in a second position, in which the injector can be operated by screw actuation.

FIGS. 3 and 4 show the injector 1 in a setting for push actuation P (FIG. 3) and in a setting for screw actuation S (FIG. 4).

In FIG. 3, the switch element 16, which is located behind the wing handle 23 on the main body 10, is brought to a rear position facing away from the wing handle 23 by turning it counterclockwise as viewed along the actuation axis 12 from the direction of the handle 32. In doing so, pins 22 on the inside of the switch element 16 run in the grooves 21 in such a way, that the switch element 16 is axially displaced by a manually introduced rotational movement about the actuation axis 12, and in FIG. 3 the switch element 16 is in the rear position widening the spring arms 14, so that the spring arms 14 with the internal thread engagement structure 15 do not engage with the external thread 13 on the actuation element 11.

To generate a radial displacement of the spring arms 14 towards the actuation axis 12, the switch element 16 features an inner cone 19, which forms part of the inner surface 17 of the switch element 16. The outer surfaces 18 of the spring arms 14 face the inner surface 17 of the switch element 16, and the outer surface 18, as well as the inner surface 17, features an inclination that extends at an angle α to the actuation axis 12. Thus, if the switch element 16 is displaced along the actuation axis 12, the inclination or slant of the inner surface 17 and the outer surface 18, which are in contact with each other, pushes the spring arms 14 radially inwards or releases them radially outwards again, depending on whether the switch element 16 is displaced in the direction of the wing handle 23 or away from the wing handle 23.

Thus, FIG. 3 shows a position of the switch element 16 with a distance to the wing handle 23, so that, by the contact of the spring arms 14 with the inner surface 17 on a larger diameter of the inner cone 19, the spring arms 14 can relax elastically, so that the injector 1 can be operated by push actuation P.

On the other hand, FIG. 4 shows a position of the switch element 16 adjoining the wing handle 23, so that the outer surfaces 18 of the spring arms 14 are in contact with a section of the inner surface 17 of the switch element 16, in which the inner cone 19 already features a smaller diameter, so that the thread engagement structure 15 is engaged with the outer thread 13 of the actuation element 11. In this way, the injector 1 can be operated by screw actuation S.

Figure 5:
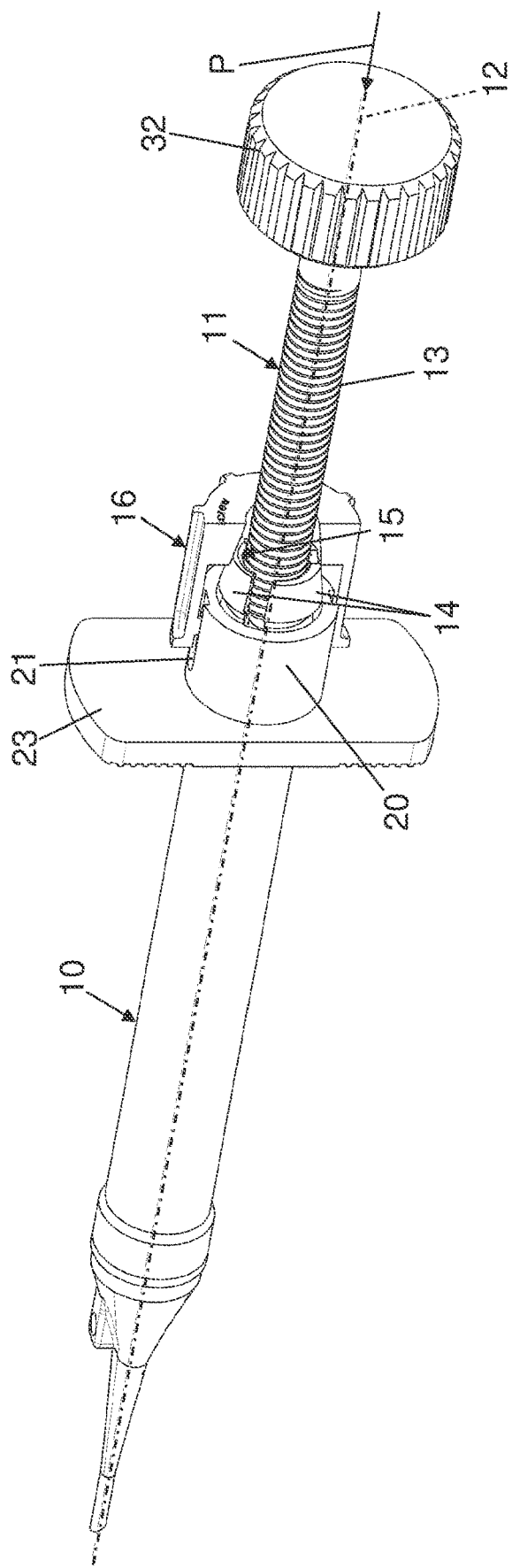
FIG. 5 a further perspective view of the injector with a cross-sectional view of the switch element, whereas the switch element is shown by an axial displacement in a first position, in which the injector can be operated by push actuation.
Figure 6:
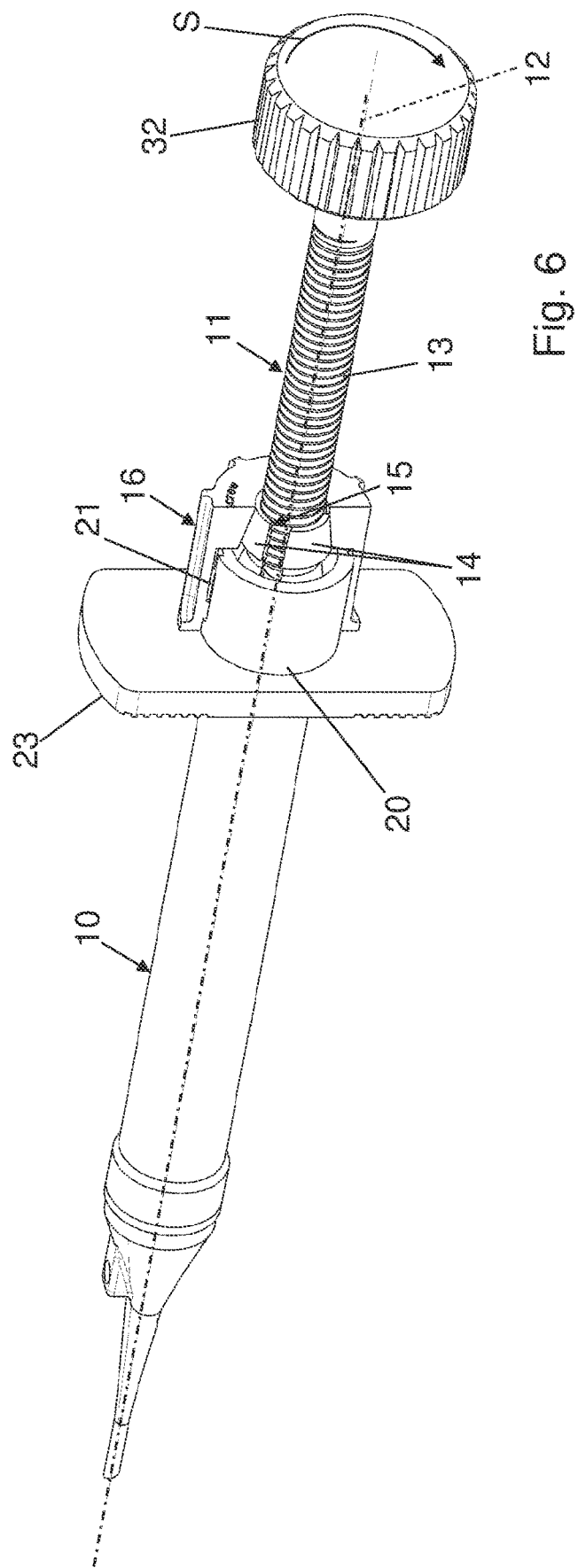
FIG. 6 the perspective view of the injector with a cross-sectional view of the switch element, whereas the switch element is shown by an axial displacement in a second position, in which the injector can be operated by screw actuation.

FIGS. 5 and 6 show another exemplary embodiment of the injector 1 with an arrangement of the switch element 16 on a receiving section 20 of the base body 10, and the switch element 16 acts on the spring arms 14 during an axial displacement as described above in such a way, that they can be brought into and out of interaction connection between the internal thread engagement structure 15 and the external thread 13 of the actuation element 11.

When the switch element 16 is set to a position as shown in FIG. 5, in which it exhibits a larger distance to the wing handle 23, the spring arms 14 spring outward, and when the switch element 16 is moved towards the wing handle 23, the spring arms 14 are pressed inwards and the thread engagement structure 15 on the inside of the spring arms 14 engages with the external thread 13 of the actuation element 11.

FIG. 5 shows the position of the switch element 16 spaced apart to the wing handle 23, so that the injector 1 can be operated by push actuation P, and in FIG. 6 the switch element 16 is shown in a position close to the wing handle 23, and the spring arms 14 are pressed inwards, so that the injector 1 can be operated by screw actuation S.

The groove 21 on the receiving section 20 runs parallel with the actuation axis 12, so that the switch element 16 cannot be rotated according to this embodiment, and it can only be moved axially by the operator between the two end positions described above, which can be designed in particular as detent positions providing a haptic feedback. This illustrates an embodiment, according to which the switch element 16 can also be designed as a slider, whereas the switch element 16 does not necessarily have to completely enclose the actuation element 11, and the switch element 16 can also be designed as a slider arranged at a circumferential position, in deviation from the representation according to FIGS. 5 and 6.

The injector 1 thus offers the advantage, that a surgeon can decide immediately before the intervention in the human eye, either by himself or via an operation assistant, whether he wants to operate the injector 1 by the push actuation P or by the screw actuation S. The handle 32 is only shown as an exemplary embodiment and can also be designed alternatively, in particular smaller. Similarly, the wing handle 23 does not have to be designed with an extension in a transverse direction, but can also be designed as a handle plate with a collar around the actuation axis 12. The embodiment shown in FIGS. 5 and 6 can also be used as a pre-load system or cartridge system.

The invention is not limited in its embodiments to the preferred embodiments given above. Rather, a number of variants are conceivable which make use of the solution presented even if the design is fundamentally different. All features and/or advantages arising from the claims, the description or the figures, including constructional details or spatial arrangements, may be essential to the invention, both individually and in various combinations.

REFERENCE CHARACTER LIST 1 injector
10 base body
11 actuation element
12 actuation axis
13 external thread
14 spring arm
15 thread engagement structure
16 switch element
17 inner surface
18 outer surface
19 inner cone
20 receiving section
21 groove
22 pin
23 wing handle
24 receiving means
25 lens cartridge
26 intraocular lens
27 receiving chamber
28 piston
29 rotary joint
30 lens guide section
31 ejection nozzle
32 handle
33 load opening
34 snapping means
P push actuation
S screw actuation
α angle

The invention claimed is:

1. An injector for implantation of an intraocular lens, comprising:
a base body;
an elongated actuation element, which projects at least partly into a rear section of the base body and which is movably guided along an actuation axis, wherein a movement of the actuation element into the base body is generated selectively by a push actuation along the actuation axis or by a screw actuation about the actuation axis, and wherein the actuation element features an external thread at least on one section; and
a switch element arranged on the base body;
wherein;
at least one spring arm is arranged at the base body, the spring arm having a thread engagement structure on an inner surface facing the external thread; and
the switch element interacts with the spring arm and is rotatable about the actuation axis or displaceable along the actuation axis, the switch element interacting with the spring arm via an operative contact, at least one inner surface of the switch element involved in the operative contact and/or an outer surface of the spring arm involved in the operative contact is formed inclined at an angle to the actuation axis, so that upon rotation or upon displacement of the switch element an elastic deformation of the spring arm towards the actuation axis and away from the actuation axis is generated, the spring arm configured to elastically spring away from the actuation axis, whereby the thread engagement structure is selectively engaged or disengaged with the external thread.

2. The injector according to claim 1, wherein:
the switch element is a sliding element and is displaceably arranged in or on the base body; and/or
the switch element is ring-shaped or hull-shaped and encloses the actuation element partially or completely.

3. The injector according to claim 1, wherein:
the switch element forms a body of rotation, which is manually rotatable about the actuation axis and which features an inner passage, the at least one spring arm projecting through the inner passage and the actuation element extending through the inner passage.

4. The injector according to claim 3, wherein:
the inner surface is formed in the inner passage of the switch element and forms an inner cone circumferentially arranged about the actuation axis, so that by an axial displacement of the switch element in the actuation axis the outer surface of the spring arm contacts with different radii of the inner surface within the switch element.

5. The injector according to claim 1, wherein:
the base body features a receiving section with a passage, through which the actuation element extends and the actuation element is movably received at or on the receiving section, whereas the at least one spring arm extends into an area between the inner surface of the switch element and the actuation element.

6. The injector according to claim 5, wherein:
the base body features a wing handle, and the receiving section adjoins the rear side of the wing handle as an extension.

7. The injector according to claim 6, wherein:
the base body is formed in one piece with the receiving section and with the wing handle made from a plastic body; and
a lens guide section with a tip-side ejection nozzle for ejecting the intraocular lens is arranged at a front end of the base body.

8. The injector according to claim 1, wherein:
the switch element is received at or on the receiving section in such a manner that the actuation element is axially movable along the actuation axis and/or is rotatable about the actuation axis.

9. The injector according to claim 1, wherein:
the at least one spring arm comprises at least one spring arm, two spring arms facing each other, or three, four or more spring arms arranged on a rear end of the receiving section or arranged at the base body in a position within the receiving section.

10. The injector according to claim 1, further comprising:
at least one groove provided in an outer circumference of the receiving section; and
at least one pin formed at an inside of the switch element, the pin being guided in the groove.

11. The injector according to claim 1, wherein:
the switch element is arranged on the receiving section by a threaded connection, so that upon rotation of the switch element about the actuation axis, the switch element performs a movement along the actuation axis so that by an axial displacement of the switch element along the actuation axis the outer surface of the spring arm contacts with different radii of the inner surface within the switch element.

12. The injector according to claim 1, wherein:
the injector features a receiving means for a lens cartridge, an intraocular lens being inserted into the lens cartridge, and the lens cartridge with the intraocular lens is insertable into the receiving means.

13. The injector according to claim 1, wherein:
the injector features a receiving chamber, which is formed in the base body and/or in a lens guide section arranged at a front end of the base body, an intraocular lens being inserted in the receiving chamber, so that the injector forms an individually manageable and tradable unit with the inserted intraocular lens.

14. The injector according to claim 1, further comprising:
a piston received in the base body, the piston being axially displaceable by the actuation element via a rotary joint.

* * * * *